United States Patent

Cameron et al.

[11] Patent Number: 5,936,739
[45] Date of Patent: Aug. 10, 1999

[54] GATED FREQUENCY-RESOLVED OPTICAL IMAGING WITH AN OPTICAL PARAMETRIC AMPLIFIER

[75] Inventors: Stewart M. Cameron, Albuquerque; David E. Bliss, Tijeras; Mark W. Kimmel, Edgewood; Daniel R. Neal, Tijeras, all of N.M.

[73] Assignee: Sandia Corporation, Albuquerque, N.M.

[21] Appl. No.: 08/791,037

[22] Filed: Jan. 29, 1997

[51] Int. Cl.[6] .............................. G01N 21/00; A61B 6/00
[52] U.S. Cl. ..................... 356/441; 359/330; 128/665
[58] Field of Search .................. 128/665; 348/31, 348/81; 356/441, 442; 250/341.1; 359/330

[56] References Cited

U.S. PATENT DOCUMENTS

| | | | |
|---|---|---|---|
| 4,146,799 | 3/1979 | Pitt et al. | 356/442 |
| 4,195,311 | 3/1980 | Moran | 348/31 |
| 5,140,463 | 8/1992 | Yoo et al. | 348/31 |
| 5,371,368 | 12/1994 | Alfano | 920/193 |
| 5,441,054 | 8/1995 | Tsuchiya | 92/996 |
| 5,528,365 | 6/1996 | Gonatas | 203/378 |

Primary Examiner—Frank G. Font
Assistant Examiner—Zandra V. Smith
Attorney, Agent, or Firm—George H. Libman

[57] ABSTRACT

A system for detecting objects in a turbid media utilizes an optical parametric amplifier as an amplifying gate for received light from the media. An optical gating pulse from a second parametric amplifier permits the system to respond to and amplify only ballistic photons from the object in the media.

11 Claims, 8 Drawing Sheets

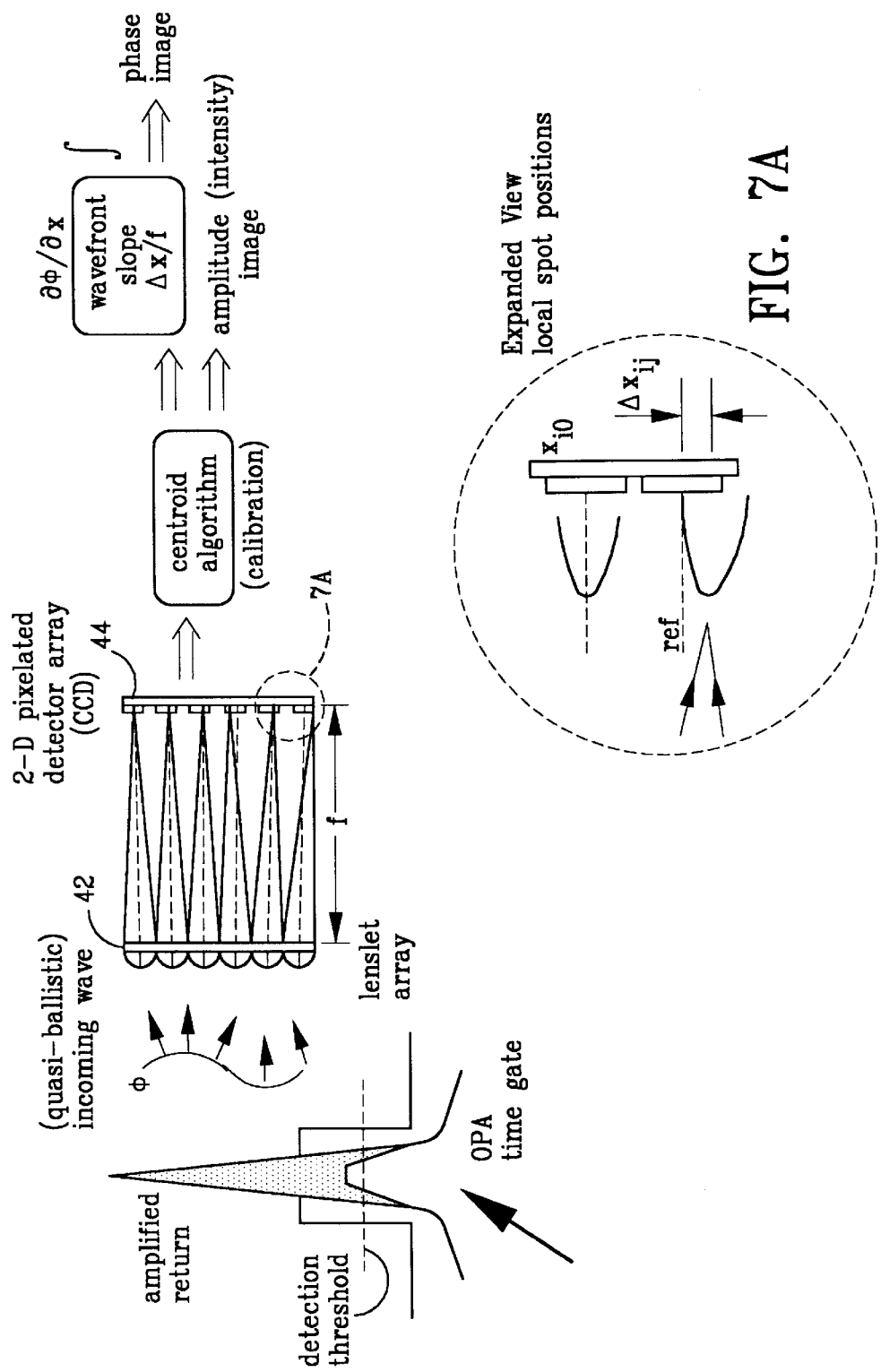

GATED FREQUENCY-RESOLVED OPTICAL IMAGING WITH AN OPTICAL PARAMETRIC AMPLIFIER

The United States Government has rights in this invention pursuant to Department of Energy Contract No. DE-AC04-94AL85000 with Sandia Corporation.

CROSS REFERENCE TO RELATED APPLICATIONS (Not Applicable)

BACKGROUND OF THE INVENTION

Noninvasive optical imaging diagnostics to quantitatively measure absorption and scattering characteristics of biological tissues are a fundamental prerequisite for a growing number of physiological monitoring procedures and preventative protocols, such as cerebrovascular oxygenation status, photodynamic dosimetry, transillumination shadowgraphy of malignant lesions, and dermatological and ocular photopathology. Although state-of-the art optical imaging performance must be substantially improved to achieve the resolution currently obtainable with conventional radiological modalities such as x-ray computed tomography (CT), positron emission tomography (PET), and magnetic resonance imaging (MRI), optical diagnostics offer unique promise of significantly lower cost and reduced instrumental complexity in acute care environments. Additionally, probing the near-infrared spectral region (600–1300 nm), or so-called "therapeutic window," is a potentially useful noninvasive paradigm for examining internal tissue histopathology owing to the relatively high penetration depths available at these wavelengths with negligible attendant risk of collateral damage from ionizing radiation.

The near-infrared is the spectral region of greatest optical transparency, but multiple scattering is pervasive in fatty tissue at these wavelengths and hinders image formation and the determination of absorption coefficients. Elastic scattering inhomogeneities originating from cellular components (chromatin, organelles, membrane interfaces, intracellular fluid, solutes such as glucose, etc.) with dimensions on the order of an optical wavelength modify the bulk index of refraction (n=1.35–1.5) and cause strong random diffusion of light. Significant temporal and spatial dispersion is induced by this random scattering process on optical pulses, and results in a broad distribution of scattering trajectories and associated pathlengths for radiation traversing the medium.

The nature of transmitted or reflected light ranges from the quasi-coherent properties of the minimally scattered component to the random incoherent light of the diffuse component. Light propagating in tissue will typically lose coherence memory after traveling only a few millimeters, as each photon on average undergoes 100–1000 scattering events with an increase in effective pathlength of over tenfold. Diffuse scatter is the main obstacle to quantitative implementation of optical imagery and tomography in turbid environments.

As opposed to conventional radiological methods, in which most x-ray photon trajectories are along the instrumental line-of-sight, optical wavelengths undergo multiple scattering. The result is a broad distribution of optical propagation delays and irregular pathlengths that degrade (or blur) underlying images and progressively scramble the geometric correlation between incident and detected light. The resulting pathlength uncertainty associated with the detected signal adversely effects the quantification of absorbance and the accuracy of range-resolved optical sensing measurements derived as a function of propagation delay time. In addition, the diffuse background level reduces the effective dynamic range and maximum penetration depths available for unambiguous object detection. Compensation for these "fog-like" effects requires dynamic path-sensitive imaging methods which rely on spatial, temporal, and phase signatures to actively discriminate against diffusely scattered light background.

Theoretically, the dielectric function (phase and amplitude image) may be reconstructed from the diffuse emission if the spatial and temporal distribution of the phase and amplitude are known simultaneously at many discrete points. However, the uncertainty of path of the detected signal makes the inverse scattering problem inherently underdetermined in the absence of deterministic constraints (restrictive assumptions) or simple boundary conditions. Computational approaches to model photon fluence propagation in highly scattering media based on the diffusion approximation to radiative transport theory and numerically intensive Monte Carlo particle-in-cell simulations have been similarly difficult to implement for realistic scenarios; i.e., a stochastic boundary condition imposed by a random interface.

Tradeoffs exist between the temporal and phase-resolved frequency domain approaches to optical imaging in multiple scattering media. The main advantage of frequency domain measurements with modulated light are the detection of the majority of the re-emitted light (diffuse) in the form of photon density waves over large penetration depths. These low-frequency evanescent waves, in contrast with electromagnetic waves, are solutions to the photon diffusion equation and are characterized by a phase velocity and modulation wavelength which are primarily functions of the optical diffusivity. However, the diffuse imaging approach relies on having a spectroscopic model for interpretation, and the diffuse character of the measurement variable makes achieving adequate spatial resolution in the image potentially problematic without the use of phased array sources in an interferometric geometry.

The basic strength of time-resolved spectroscopy is that no mathematical manipulation is needed to interpret raw data, as the photon signal reveals the full time-domain distribution of photon travel (time-of-flight) and explicitly determines scattering and absorption properties. In the time domain approach, pathlength is explicitly determined for each detected photon rather than an ensemble average, resulting in good spatial localization at the expense of the small signal size associated with measuring only the coherent component. Additionally, all-optical time domain techniques allow examination of sampling timescales corresponding to gigahertz frequencies inaccessible by current frequency domain techniques, albeit at the expense of the instrumental complexity associated with ultrashort optical technology. However, the instrumentally challenging aspects of short pulse generation and its associated expense has been considerably reduced by recent innovations in diode laser design and integrated optics.

Ballistic imaging is a path-sensitive coherent imaging approach designed to overcome the negative effects of turbidity on traditional line-of-sight methodologies by exploiting the influence of scattering inhomogeneities on the temporal dynamics of photon diffusion. An ultrashort light pulse travelling through a discrete random medium is temporally dispersed into two components each characterized by uniquely different optical signatures. The first (ballistic)

component is strongly attenuated and comprised of those minimally scattered transmitted photons which result from coherent interference of light scattered in the forward direction. These so-called ballistic photons propagate essentially undeviated from the incident straight-line trajectory and carry the least distorted image information and the highest degree of spatial localization regarding optical absorption. The second component encompasses the majority of re-emitted photons and results from incoherent multiple scattering associated with a diffusive random walk process through the intervening medium, and it subsequently appears as off-axis background noise (blur) in the image plane. The time-gated ballistic imaging approach seeks to isolate the early-arriving ballistic image-bearing component from the adverse effects of diffuse scattering on image formation using an ultrafast optical gate, typically less than 50 picoseconds in duration, superimposed on the transmitted photon time-of-flight distribution. Temporal gating rejects or filters out the much larger number of late-arriving photon trajectories resulting from the incoherent diffuse scattering distribution through the medium, thereby eliminating optical pathlength uncertainty over the gate interval.

Pictorially, the signal intensity measured over the gate width (integration time) which emerges from the sample depends on the inherent absorption and scattering properties within an approximately ellipsoidal volume oriented along the transillumination axis. The spatial extent of the ellipsoid is constrained by the volume of all photon paths which are possible in a given time-gated interval, and the size of each traversal section or time slice $\pm\delta\tau=n\delta L/c$ of the volume represents the resulting spatial resolution of the image.

Numerous experimental methods have been demonstrated to implement the requisite temporal discrimination, including optical shutters based on transient nonlinear Kerr, photorefractive, or stimulated Raman interactions, "light in flight" interferometric and cross-correlation heterodyne/homodyne gating based on field coherence properties, electronically gated streak camera imaging, and time-correlated single photon counting. Ballistic imaging techniques such as these can achieve close to diffraction-limited resolution but suffer from extremely small signal levels due to the selective nature of the time-gating process which discards the bulk of the illumination energy to achieve maximum contrast. Moreover, since the intensity of the time-gated coherent component is attenuated approximately exponentially with penetration depth and scattering mean-free-path, general applicability is fundamentally restricted in thick scattering media by operational compromises between measurement sensitivity (minimum detectable signal), dosimetry limitations (damage threshold), and image contrast (gate width) criteria.

The ability to image through dense scattering medium is fundamentally limited by the sensitivity to small ballistic and quasi-ballistic signals, as the intensity of the coherent component is attenuated approximately exponentially with thickness and scattering mean free path. Achievable image quality is a subjective compromise between minimum detectable signal and the relative size of the diffuse component. The gate should provide substantial discrimination against the time-delayed diffusively scattered light which contains the bulk of the pulse energy, while maintaining high transmission efficiency of the image-bearing component for maximum dynamic range. Shorter gate durations imply better image contrast and improved spatial resolution, but at the expense of fewer integrated photons for signal processing. An optimum integration time has to be determined between a blurred dc image (integration time too long) and a noisy image (integration time too short). The minimum detectable transmission level for ballistic imaging is fundamentally limited by the quantum shot noise of the detector, and the maximum permissible number of input photons impinging on the tissue sample is limited by dosimetry constraints determined by the ANSI exposure standards and FDA ocular safety guidelines.

Based on these considerations and typical tissue parameters, a transillumination imaging system for biological tissue should ideally be capable of detecting spatially-resolved images over a dynamic range of transmitted signal exceeding twelve orders of magnitude. The laser source should generate low-noise stable optical pulses at kilohertz or higher repetition rates and deliver ~25 mW average powers to achieve illumination fluences adequate for image contrast over a range of penetration depths (centimeters) while maintaining sample exposure levels below the burn standard for living tissue. The source should possess wavelength versatility for spectroscopic imaging, and produce the pulse durations necessary to achieve millimeter spatial resolution with sufficient power for nonlinear gating of full 2-D images. Fast sampling achievable with mode-locked pulse trains combined with a noiseless amplifying gate could partially compensate for the extremely low number of photons integrated over a short gating periods by improving image processing rates, and minimizing the effect of dark noise statistical fluctuations on photon counting precision and radiometric fidelity of photodetector arrays. Image processing speed is essential for medical diagnosis under conditions where the measurement must be performed rapidly compared to movement of the subject (i.e., motion-induced artifacts due to breathing).

Ballistic imaging has been mentioned in a few U.S. patents prior to this invention. U.S. Pat. No. 5,371,368 of Alfano et al discloses a system for ballistic imaging an object in or behind a highly scattering medium which utilizes a large laser and a Kerr gate. U.S. Pat. No. 5,441,054 of Tsuchiya discloses a detection system utilizing phase modulation, but no amplification, of the detected signal. This patent notes that ballistic imaging is difficult due to weak signals. U.S. Pat. No. 5,528,365 of Gonatas compares the spatial distribution of photons scattered by an object to the calculated flux for a homogeneous object to yield the optical structure of the object convolved with a computed probability weighting function, from which a tomographic map of the object can be obtained. None of these patents teaches the novel use of a parametric amplifier in a ballistic imaging application.

SUMMARY OF THE INVENTION

It is an object of this invention to provide a system for ballistic imaging which overcomes the disadvantages set forth above.

It is another object of this invention to provide a system for ballistic imaging using optical parametric amplification.

Additional objects, advantages, and novel features of the invention will become apparent to those skilled in the art upon examination of the following description or may be learned by practice of the invention. The objects and advantages of the invention may be realized and attained as particularly pointed out in the appended claims. To achieve the foregoing and other objects, and in accordance with the purpose of the present invention, as embodied and broadly described herein, the present invention may comprise a system for detecting objects in a turbid media including a laser or similar device for directing a pulse of radiant energy into the media; a first optical parametric amplifier for receiving energy from the media; a very short gate signal formed preferably from a second parametric amplifier for applying a gating signal to said gate means, wherein said gate means is responsive only to ballistic photons from said media; and an output detector for detecting an output from said amplifier.

BRIEF DESCRIPTION OF THE DRAWINGS

The accompanying drawings, which are incorporated in and form part of the specification, illustrate an embodiment of the present invention and, together with the description, serve to explain the principles of the invention.

FIGS. 7 and 7A show wavefront sensing with a binary optic sensor incorporated into the invention.

DETAILED DESCRIPTION OF THE INVENTION

Figure 1A:
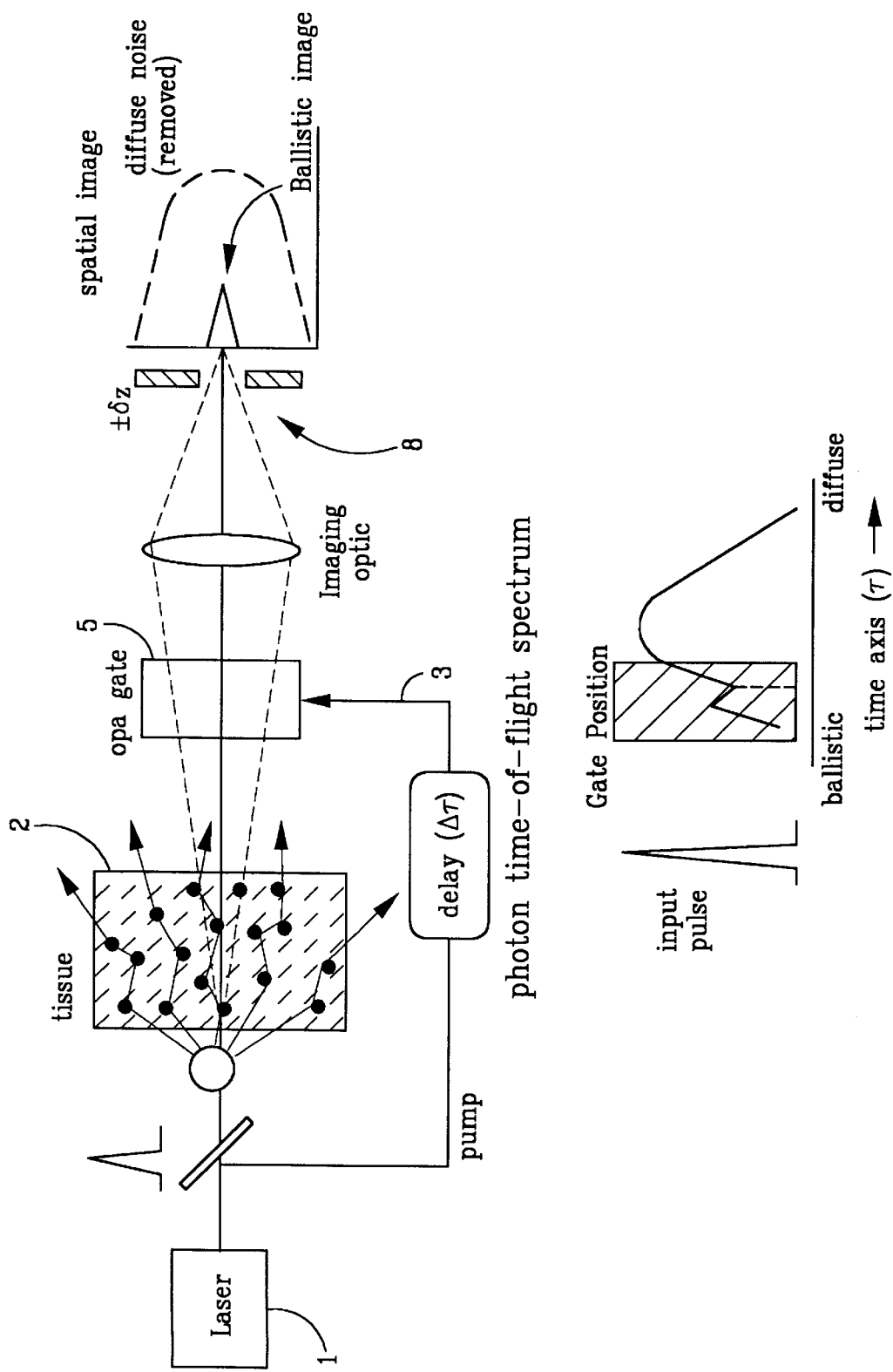
FIG. 1A shows a schematic representation of the system of this invention.

FIG. 1A shows an embodiment of this invention to include a source of radiant energy such as laser 1 providing such energy into a turbid media 2 which may be human tissue, fog, a murky liquid, or the like. A wavelength-tunable, ultrashort amplifying gate 5 which includes a parametric amplifier is gated by a signal 3 to receive only ballistic photons passing through media 2. The output of gate 5 is provided to an imaging detector 8.

Parametric amplification, also referred to as difference mixing generation, is of particular interest not only because it is a high gain process but also because the time during which amplification occurs can be effectively limited by the duration of an applied pump (gating) pulse. A short-pulse optical parametric amplifier is capable of ultrafast temporal gating, direct two-dimensional image acquisition, and spectral conversion over a broad wavelength range defined by the signal/idler tuning curve, quantum sensitivity approaching one photon per spatial resolution element, and a high degree of coherent discrimination against diffuse light obscuration of image quality.

Figure 1B:
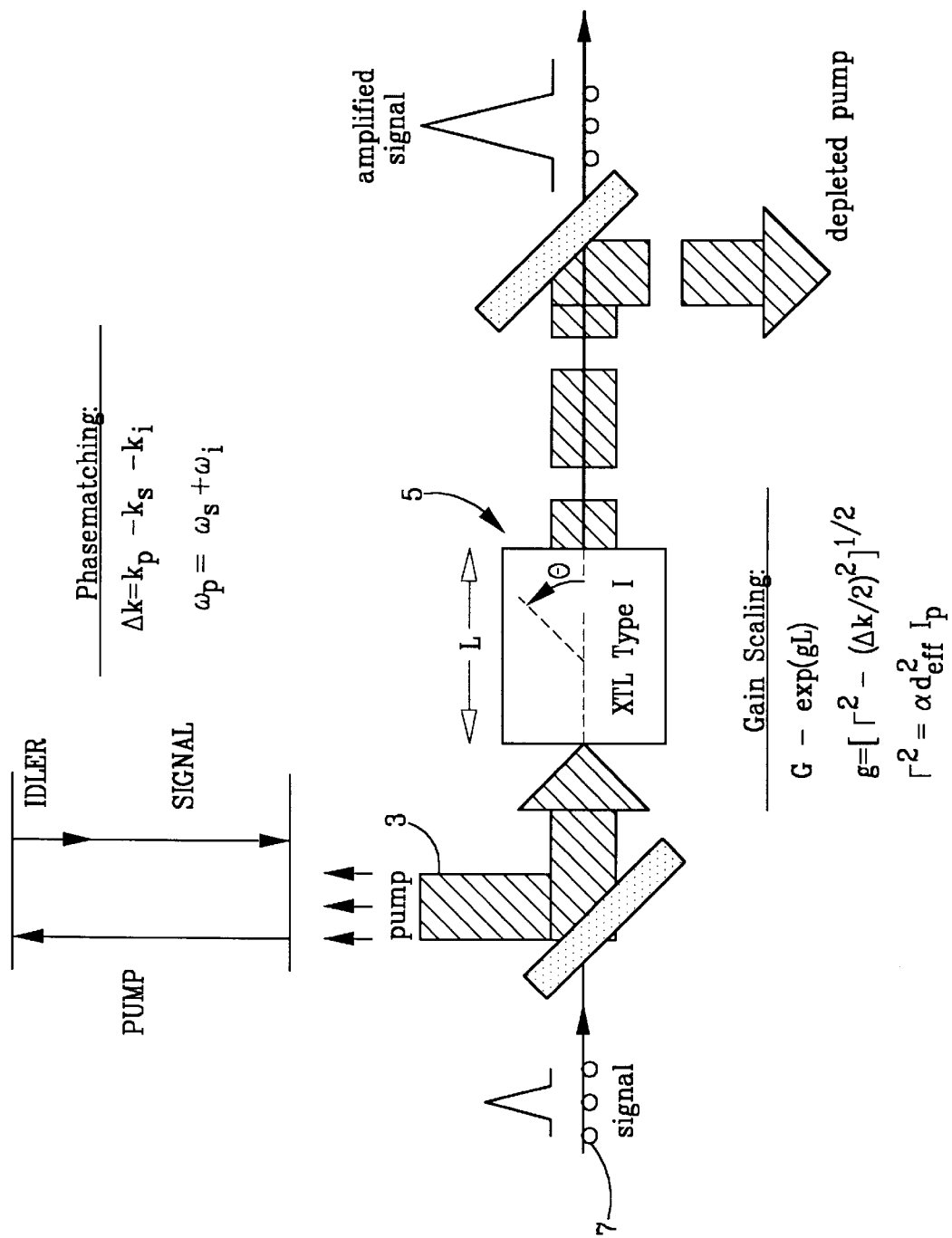
FIG. 1B shows a representation of a parametric amplifier utilized in the system of FIG. 1A.

As indicated in FIG. 1B, the gating mechanism involves the temporal and spatial overlap of a strong reference (gating) beam 3 with an attenuated image-bearing probe beam 7 in a phasematched nonlinear crystal of parametric amplifier 5 to produce gain via a three-wave parametric interaction. In this process, each incident pump photon pairwise generates two tunable lower frequency photons (denoted signal $\omega_s$ and idler $\omega_i$) having gain scaling dependent on the crystal interaction length (L) and nonlinearity ($d_{eff}$), pump intensity ($I_p$), and phase mismatch ($\Delta k$). The gate acts as a noiseless image intensifier (in the absence of spontaneous parametric scattering) to simultaneously amplify and temporally isolate the weak quasi-ballistic or early-arriving, partially coherent, component of the transmitted light. Gain in amplifier 5 exists for approximately the duration of the pump pulse. The nature of the nonlinear optical coupling, primarily the time correlation, angular acceptance, and phasematching, provides temporal, spatial, and polarization discrimination against diffusely scattered background light. The resultant image is observed directly at the injected probe frequency (image amplification) or, alternatively, on a zero background at the spectrally converted difference frequency between pump and probe (sideband image upconversion).

Time-gated parametric amplification exhibits low noise and high sensitivity, with gains in excess of $10^4$ achievable for low incident light levels. Broad wavelength tuning can be accomplished by systematic variation of the crystal phasematching conditions to minimize momentum mismatch and maximize gain. Depth profiling is accomplished by using a filtered backprojection CT algorithm to reconstruct the three dimensional image, as is well known to those skilled in this art. The lateral image spatial resolution is determined by the spatial magnification of the gating pulse for the specific crystal focusing geometry defining the gain region. Contrast of the gate is defined by the ratio of light transmitted when the reference beam is present to the off condition.

Figure 2A:
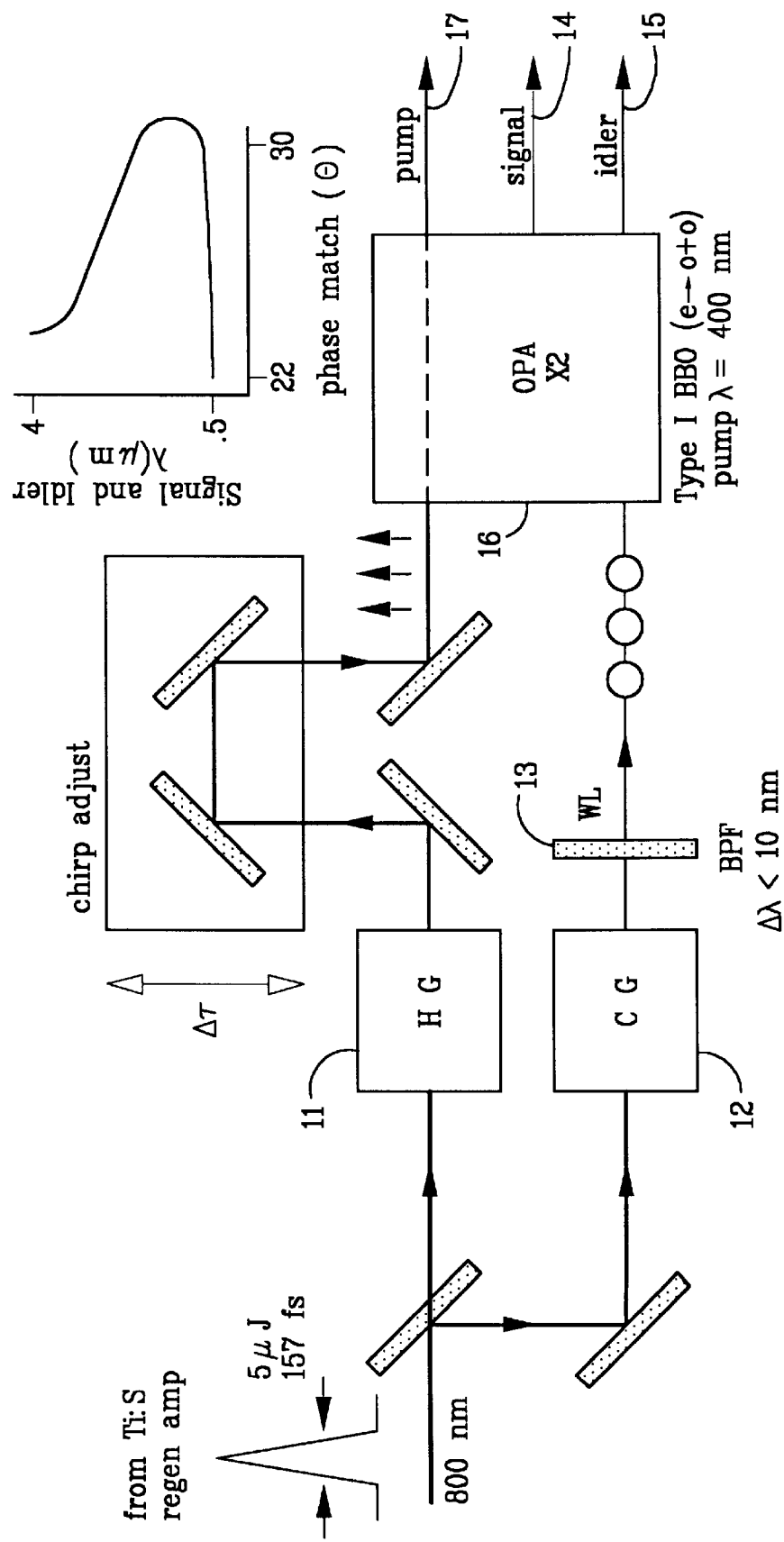
FIGS. 2A and 2B show a second embodiment utilizing cascaded parametric amplifiers.
Figure 2B:
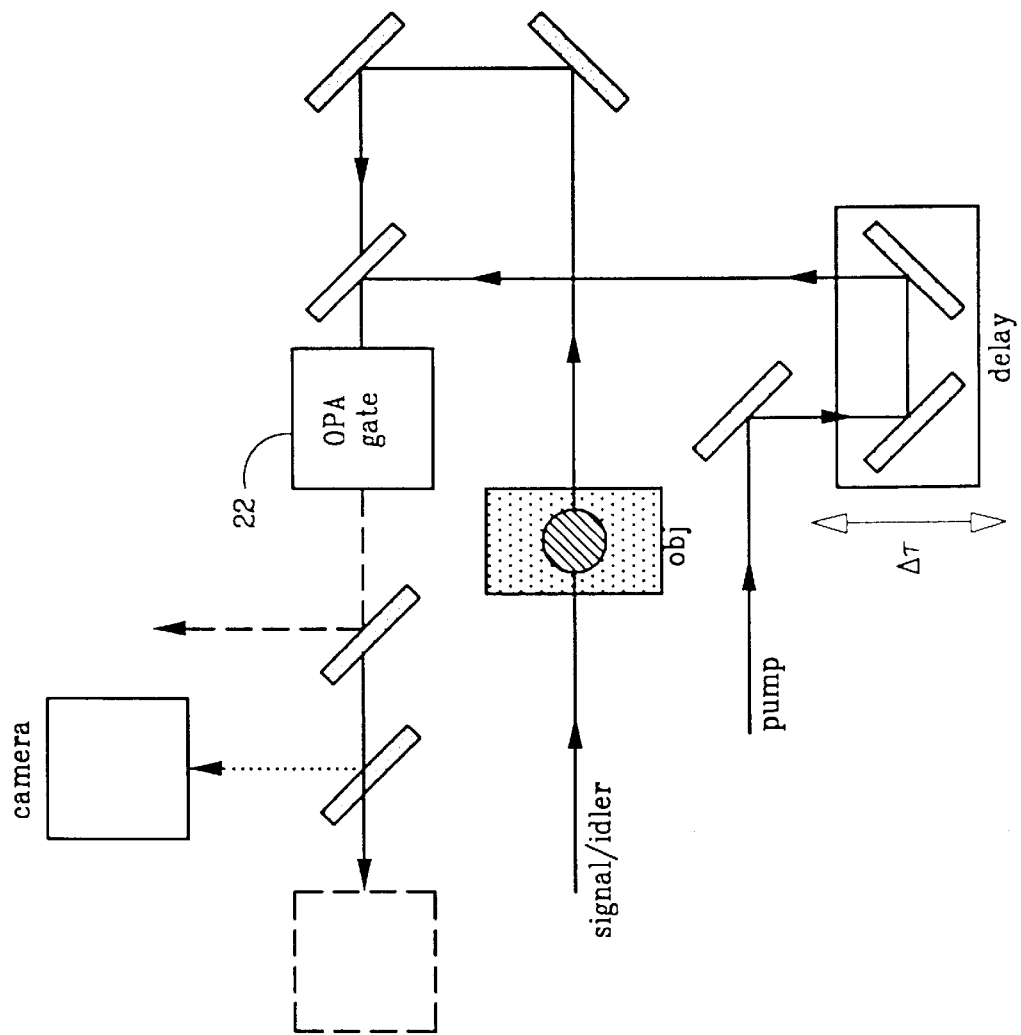

Femtosecond parametric amplification of a monochromatic near- infrared image in a β-barium borate (BBO) type I (e→o+o) crystal ($\theta=29°$) placed at the image plane has been performed. This embodiment of the invention utilizes two cascaded micro-joule BBO optical parametric amplifiers (OPA), one as a tunable coherent light source 16, as shown in FIG. 2A, and the second as a quasi-ballistic gate 22 placed after the test object, as shown in FIG. 2B. The probing wavelength is derived from either the signal 14 or idler 15 branches of first OPA 16, and, to avoid timing jitter, both stages are sequentially pumped by second harmonic light 17 (type I lithium triborate $\theta=28°$, $\phi=90°$) from a regeneratively amplified titanium sapphire laser operating at a 250 KHz repetition rate near 800 nm and passing through harmonic generator 11. A broadband white light continuum generator 12 and adjustable bandpass filter 13 seed first amplifier 16 and afford efficient spectral tuning from 470–750 nm in the signal and 0.94 to the absorption edge of BBO near 2.4 μm in the idler, excluding the region near degeneracy.

Amplifier 16 is operated in a double pass collinear configuration to compensate for group velocity mismatch (GVM) effects between the pump and signal/idler waves. Gains approaching 1000 over the white light background level are possible with proper pump energy distribution in each pass. To attain these gain levels, the first pass is adjusted to weakly saturate the amplifier so that the second pass extracts about 10–20% of the total pump energy.

A collinear geometry minimizes $\Delta k$ mismatch detrimental to image formation which occurs in crossed-beam optical geometries. The spectral output is tuned by rotating the crystal about its phasematching axis and varying the white light delay (chirp) to allow appropriate wavelengths to temporarily overlap the pump. For type I phasematching, the pump and signal (or idler) waves are orthogonally polarized. Dichroics and bandpass filters are used to separate pump and probe wavelengths with good spectral purity. Typically, the signal branch exhibits 100–200 nJ pulse energies, ~157 fs pulsewidths, and 5–25 nm bandwidth as a function of wavelength, with lower energies and slightly longer pulses for the idler. Spatial mode quality is characterized by a Gaussian $M^2$ value better than 1.5. The nominal crystal interaction length (1 mm) in both amplifiers is chosen to minimize spatial ($\theta$dL) and temporal walk-off (L<$\tau\Delta$vg) and the input confocal parameters ($w_o$~80–100 $\mu$m, $z_R=\pi w_o^2/\lambda$~0.5 mm) are adjusted for maximum spatial overlap, efficient gain, and optimum angular acceptance, subject to the self-focusing damage threshold (<50 GW/cm$^2$). Pump energy requirements of the parametric process are modest ($\mu$J) and are obtainable with current generation diode-pumped oscillator/regenerative amplifier configurations.

The aforementioned system was benchmarked to reconstruct and enhance test images with absolute feature sizes of 65 $\mu$m/mm$^2$ in background optical attenuations exceeding $10^{12}$. Two-dimensional amplified ballistic images of a standard Air Force resolution chart embedded between opal diffusers simulating random media were obtained for various attenuations and exposure times less than 10 seconds using a liquid nitrogen cooled 1024×1024 detector array. These diffusers are basically nonabsorbing Lambertian scatterers which attenuate the useful component of the image-bearing light by randomizing the distribution of photon paths traversing the sample and by deflecting light (via multiple scattering) from the optic axis and field-of-view of the gate. Thus the effect of the diffuser is to both effectively attenuate the beam approximately eight orders of magnitude for 2 mm of diffuser thickness, and to completely obscure any underlying image information by producing a strong diffuse afterglow or scattering halo. It should be emphasized that this process is an entirely different effect than simply attenuating the intact coherent beam; here the image is not recoverable with standard line-of-sight techniques.

Assuming absorption is negligible in the opal diffusers compared with the effects of diffuse scattering, the maximum measured optical density or extinction corresponds to nearly 28 scattering transport lengths; i.e., exp(−28)=exp(−$\mu_t$L). Although opal diffusers are not extended sources with a continuous variation in dielectric constant as would be the case in tissue media, the achievable dynamic range is nonetheless a significant advance for biomedical imaging applications. Presupposing an inverse transport length of ~1 mm$^{-1}$ ($\mu_t=\mu_a+\mu_s'$), which is a reasonable average value for fibroglandular tissue, and noting in the quasi-ballistic detection case, $$\mu_t(\lambda)=\mu_a(\lambda)+\mu_s(\lambda)=z^{-1}\ln(I_o/I_{trans}),$$

this level of attenuation corresponds to a physical penetration depth (z) greater than 3 cm.

The primary difference between tissue media and an analogous boundary diffuser will occur in the scattering anisotropy factor g~<cos$\theta$> and in the width of the temporal distribution of the transmitted photons. Tissue exhibits both significantly more forward scattering (g~0.9) and an extended optical pathlength (relative to scattering length) in comparison with an isotropic edge scatterer like opal (g<0.5). The temporal dispersion resulting from propagation in tissue would be much wider, typically ~1 nanosecond versus <150 ps in the opal diffuser case, and the early-arriving component would be comprised of fewer, if any, ballistic photons, mandating the use of a wider time-gate or larger gate acceptance angle (FOV). In addition, the size distribution of scattering centers in the opal diffuser is much more uniform and predominantly Rayleigh-like, whereas living tissue is inhomogeneous and more Mie-like in its scattering properties.

Another advantage of an OPA device in this application is that the difference frequency in the device can provide gain as well as versatile spectral tuning by virtue of the parametric coupling process between incident optical fields. Gain can be detected directly at the incident sampling wavelength or at the complimentary spectrally converted sideband. A key advantage of combining amplification and spectral conversion functions in a single parametric gate is the ability to perform imaging at longer infrared idler wavelengths less susceptible to diffuse scattering within the water window, without sacrificing the capability for efficient amplified detection at signal wavelengths within the silicon photocathode response envelope (<1100 nm). Many of these infrared wavelengths are sensitive to vibrational overtones and combination bands (OH,CH,NH) specific to metabolic changes associated with carcinogenesis and tumor pathology. Wavelength tunability will be an important aspect for optimizing absorption and scattering properties for maxuimum image contrast and detection of weak chromophores. Because the scattering coefficient appears in the exponential, small changes in its value can have a dramatic impact (orders of magnitude) on the number of available ballistic or early-arriving photons over long pathlengths in turbid media. Since the maximum permissible exposure to laser radiation increases at longer wavelengths in biological tissue higher fluences are available for imaging or alternatively, for reduced exposure times.

A cascaded experimental geometry consisting of a tunable light source based on parametric amplification in conjunction with a second OPA-based temporal gate following the illuminated object allows full flexibility in designing an imaging system for turbid environments while matching favorable transmission windows and wavelength-dependent particle size effects in the Mie scattering function. This versatile approach was demonstrated conceptually in the laboratory with the previously described optical system using wavelengths pertinent to biomedical spectroscopy. By using the second optical parametric amplifier to simultaneously amplify and spectrally upconvert (difference mix the idler and visible pump wave) an infrared idler ($\lambda$~1.3 $\mu$m) transmitted through the sample from the first stage, background effects were substantially suppressed, diffuse scattering ($\sigma_{scat}$~$\lambda^{-1}$) within the sample volume was reduced, image formation was enhanced, and detector dynamic range improved by shifting to visible signal wavelengths ($\lambda$~580 nm). A key advantage of this approach is the ability to perform spectral imaging at longer wavelengths within the water window which exhibit relatively low scatter while maintaining the capability for efficient detection. Many of these infrared wavelengths are sensitive to vibrational overtones specific to metabolic changes associated with carcinogenesis and tumor pathology. Wavelength tunability is an important aspect for optimizing absorption and scattering properties for maximum image contrast. In addition, because the scattering coefficient appears in the exponential, small changes in its value can have a dramatic impact on the number of available ballistic photons over long pathlenths. Since the maximum permissible exposure to laser radiation increases at longer wavelengths, higher fluences are available for imaging or alternatively, for reduced exposure times.

Figure 3A:
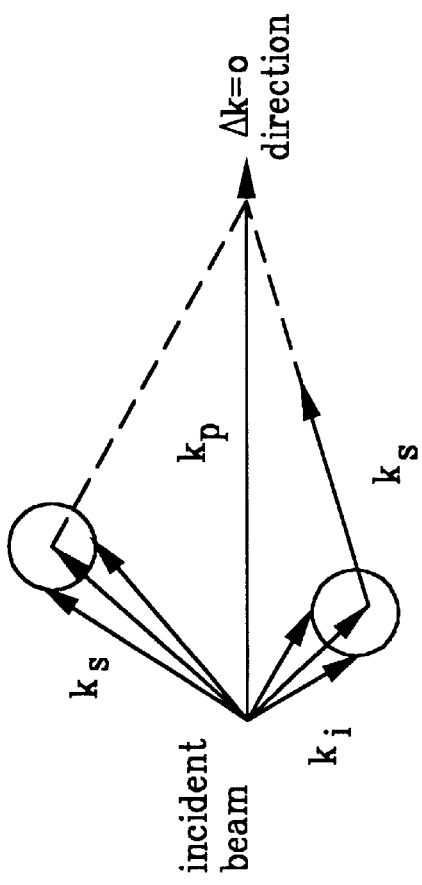
FIGS. 3A and 3B show, respectively, three-wave phasematching geometries for noncollinear and collinear diffractive imaging.
Figure 3B:
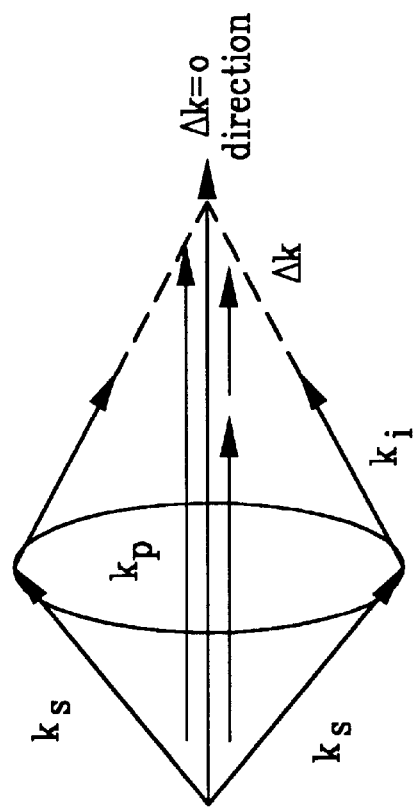

Imaging resolution characteristics of an optical parametric amplifier can be understood by considering the role of phasematching conditions in the spatial frequency domain. Each spatial frequency in the amplified bi-dimensional image, represented in FIGS. 3A and 3B as a set of signal fields with k-vectors at varying angles to the pump beam, can be associated with a plane wave that propagates in a particular direction in the nonlinear gating crystal. The distribution of spatial frequencies comprising the overall plane wave superposition is then mapped by coherent diffraction to an optical transfer function incorporating the phasematching bandwidth. Parametric amplification is restricted to a small range of k-vectors by phasematching which results in the formation of a passband in the transfer function. In this sense, an optical parametric amplifier acts as a "soft" confocal aperture for spatial amplification, with the gain passband rolling off with increasing $\Delta k$ corresponding to higher-order diffraction orders of the signal relative to the pump direction. Plane waves corresponding to nonzero spatial frequency are not phasematched and experience less gain. By analogy to pinhole diffraction theory, the clear aperture (D) is defined by the focusing geometry optimized for crystal acceptance angle $\Delta\theta=(4\pi/L)(\partial\Delta k/\partial\theta)^{-1}$, and the size of the gain region determines the spatial frequency cut-off $v_o \sim D/\lambda$ for image formation. The number of resolution elements of the amplifer is determined by the Fresnel number $N=(A/\lambda L)^2$, and since the gain of the gate is proportional to pump intensity (power over illumination area $A \sim D^2$), the number of resolution elements at fixed gain is ultimately determined by the pump power.

Figure 4A:
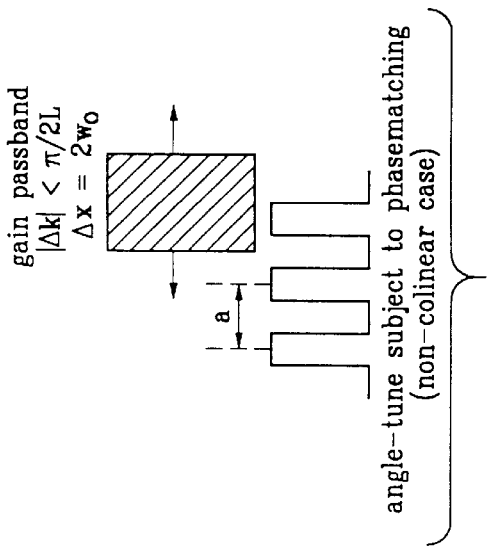
FIGS. 4A and 4B show relay imaging and the image plane therefrom.
Figure 4B:
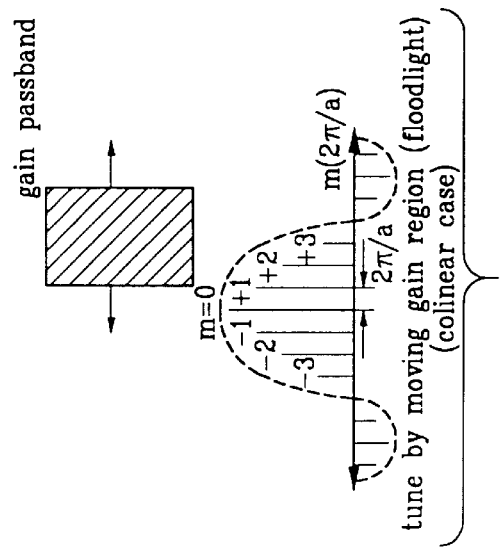
Figure 4C:
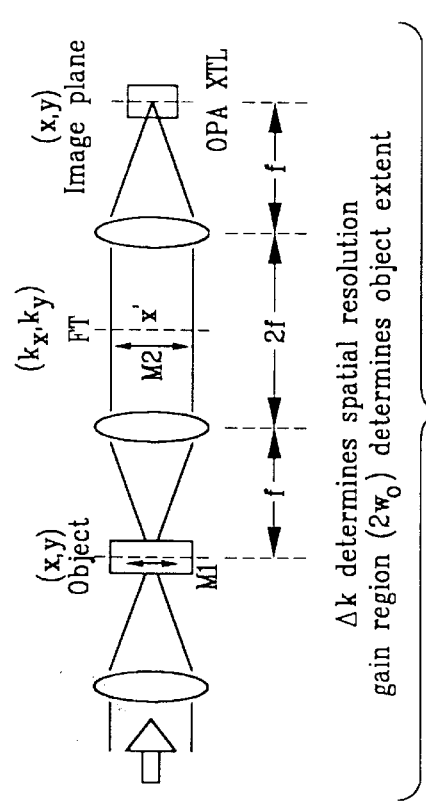
FIGS. 4C and 4D show Fourier imaging and the Fourier plane therefrom.
Figure 4D:
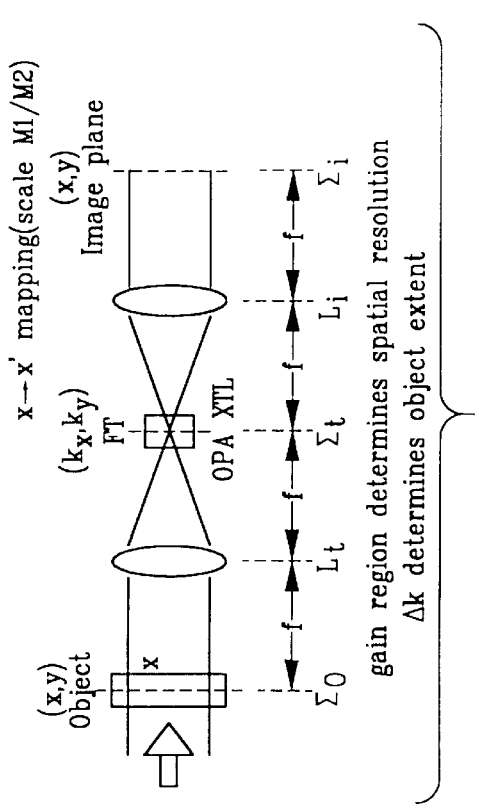

Efficiency of amplification and transfer of spatial frequencies can be described by an optical transfer function (OTF) in terms of $\Delta k$ mismatch, propagation vector, gain, and crystal length. The optical transfer function formalism is a mechanism for image quality evaluation which provides a complete description of the object-image relation in terms of its effect on the Fourier decomposition of the object intensity pattern. In the context of optical systems theory, the OTF is the Fourier transform of the point spread representation of the energy distribution in the focal plane of an imaging system illuminated by a uniform plane wavefront. The gain passband in the transfer function of an OPA is defined by the convolution of the gain region, principally the pump spot size, and the phasematching acceptance bandwidth $\sim|\Delta k|<\pi/2L$. This passband acts as an apodizer in the full wavevector spectrum and establishes a direct linkage between angular phasematching condition and spatial resolution. As a result, when the OPA gate is placed in the Fourier transform plane of the image, as shown in FIG. 4C, the output field is limited in extent by the effective phasematching aperture and exhibits a resolution related to the lateral size of the pump beam, as shown in FIG. 4D. In a relay imaging configuration shown in FIGS. 4A and 4B, such as microscopy, the roles of the previous case are reversed and resolution can be improved at the expense of field-of-view by adjusting the overall magnification of the imaging system. Outside of this narrow region, transfer functions for both the signal and idler components are relatively constant over all spatial frequencies within the acceptance angle.

Figure 5:
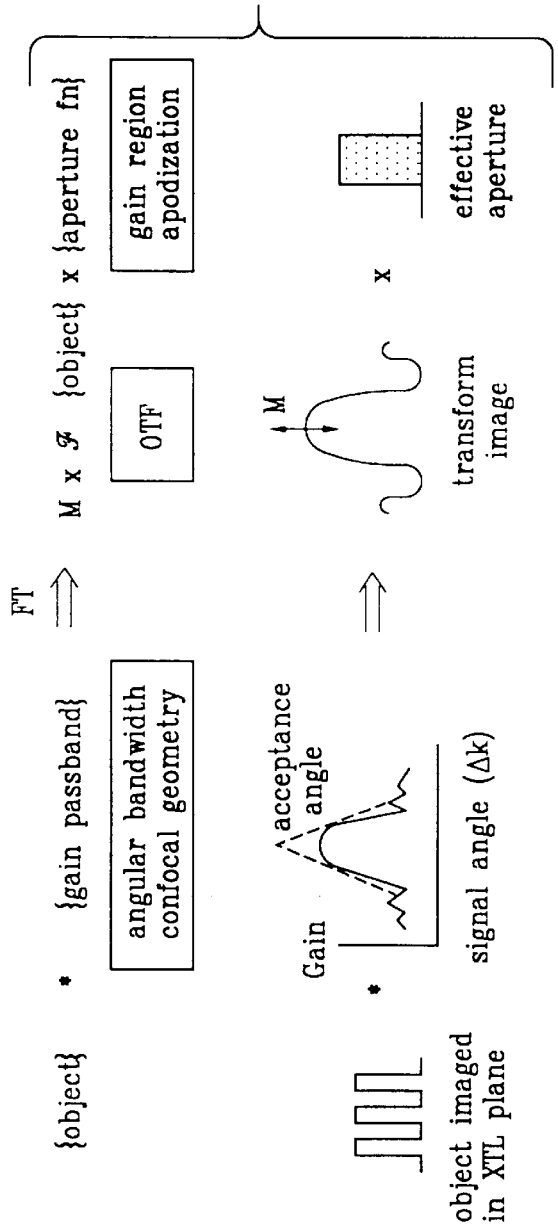
FIG. 5 shows the physics of the object-image transformation process in the Fourier transform plane of an OPA.

The optical transfer function of spatial frequencies was directly measured in the optical parametric amplifier of this invention by recording the Fourier plane image of a three-bar pattern with known spacing through the gating system. By moving the CCD camera from the conjugate image plane to an image focal plane (FT plane), either an amplified image or its corresponding spatial frequency spectrum could be clearly observed with suitable magnification. The mathematical physics describing the object-image transformation relationship through a parametric amplifier is illustrated in FIG. 5. The spatial frequency response data was normalized and compared to a theoretical fitting function of form $F_3(\omega)=\sin(6\pi x_1\omega)/(2\pi\omega\cos\pi\omega x_1)$ which is known to be characteristic of an idealized three-bar distribution ($x_1$ spacing); the cosine wave amplitude was normalized to the DC level.

Figure 6:
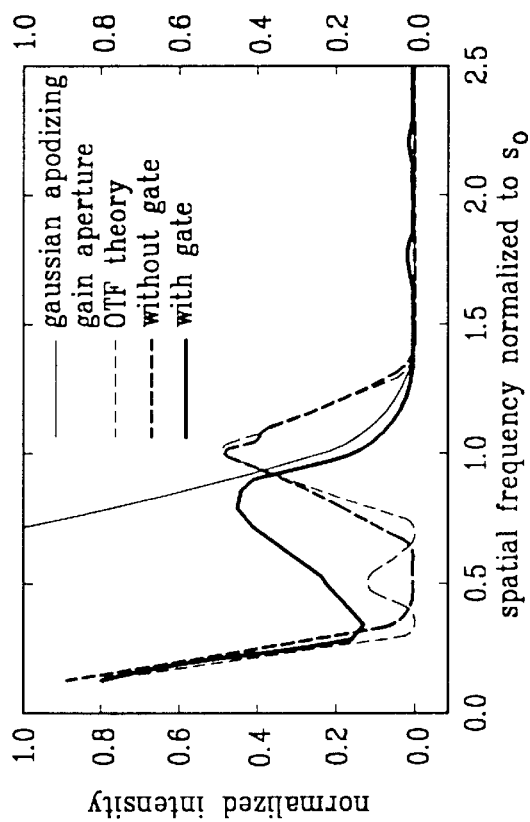
FIG. 6 shows measured optical transform function through an OPA-based imaging system of the invention.

As displayed in FIG. 6, the response of the parametric gate shows both amplification and instrumental apodization originating from the gain bandwidth, when juxtaposed with the theoretical model. The observed cut-off frequency vo was approximately 7.1 line pairs per millimeter. A slight astigmatism due to the walk-off plane caused there to be a difference in spatial resolution between vertical and horizontal directions (aspect ratio of 7/11).

Binary optics are hybrid optical elements exhibiting controllable refractive and diffractive imaging properties. The binary fabrication process derives its name from a multilevel processing sequence wherein discrete phase-encoded $2^N$ surface relief structures are patterned by integrated circuit (VLSI) manufacturing methods using iterative photomasking and etch steps. These planar phase profiles can then be used to manipulate optical wavefronts and perform agile beam steering in diverse applications ranging from amacronic focal plane sensors and aperture multiplexers, to optical interconnects (transfer optics) for photonic devices and focal plane efficiency enhancement. The arbitrary nature of the fabrication process allows essentially unlimited flexibility in constructing customized lenslet arrays as simple robust miniaturized replacements for conventional optical systems and for the creation of new unconventional components in innovative multipurpose sensors. Micro-optical devices based on this technology can be integrated with other elements such as diffraction gratings and CCD cameras to build combined spectral, intensity, and phase imaging systems which simultaneously focus and disperse light over arbitrary pupil shapes. Over the past decade, technology has sufficiently advanced to allow production of diffractive elements, hybrid refractive-diffractive elements, and refractive microoptics which are satisfactory for use in cameras, military systems, and medical instrumentation.

Phase measurement capability will be a useful complement to ballistic imaging when refractive index variation is the dominant optical response mechanism, as in the case of translucent objects with weak absorptive contrast, turbulent shear boundaries, thermoclines, or wake fields produced in the vicinity of moving objects. As taught by U.S. Pat. No. 5,493,391 of D. Neal et al. entitled, "One Dimensional Wavefront Distortion Sensor Comprising a Lens Array System", a self-referencing wavefront sensor using a 40×32 lenslet array (250 $\mu$m pixel diameter) based on binary optics technology has been developed which is sensitive to optical path distortions (OPD) approaching $\lambda/100$ and exhibits dynamic grayscale range exceeding $10^4$. By incorporating such a device to measure the wavefront slope (phase gradient) and amplitude of the range-gated OPA output, it is possible to simultaneously acquire phase and intensity maps of the dielectric function of an obscured object in low-visibility or turbid backgrounds.

Hartmann sensing offers a simple method for measuring the optical phase and intensity of laser light that has been transmitted through an aberrating medium without recourse to interferometry. As shown in FIG. 7, a Hartmann sensor consists of binary optic lenslet array 42 with a pixelated camera 44 at focal length ($f$), and a centroid algorithm that accurately locates the positions of focal spot intensity patterns recorded by the camera. The impinging wavefront field is dissected by an array of transmissive lenslets $\{i\}$ which focus the incoming light within each subaperture onto the image plane. The sensor works on the principle that focused spots xij in the back focal plane of the microlens array will be deflected a distance $\delta=x_{ij}-x_{i0}$ away from their respective optical axes due to aberrations in the optical beam. For a given incoming spherical wave the measured tilt is approximately a linear function of position along the sensor array for small-angle sampling. Because light propagates in a direction normal to the wavefront, the deflection distance is proportional to the local derivative or slope $\theta \sim \delta/f$ of the optical wave front impinging on the lenslet array. Detecting the centroid position measures the gradient of optical phase along the detector axis that is subsequently integrated to yield the optical phase distortion experienced by the beam relative to a calibration file. A digital phase reconstruction algorithm is utilized to construct a map of complex field phasors defining the full phase front $\phi(j)$ across the measurement aperture and associated moments can be projected on a Zernike polynomial basis set. Sensitivity of the Hartmann sensor is determined by the smallest tilt differential $\Delta\theta$ that the sensor can measure between successive lenslets. Knowing the complete scalar field of the beam will facilitate detailed predictions of actual beam characteristics along its propagation path through the intervening medium.

The particular sizes and equipment discussed above are cited merely to illustrate a particular embodiment of this invention. It is contemplated that the use of the invention may involve modifications of the inventions such as having the laser and detector on the same side of the dispersive media, and detecting objects in the media from reflected photons. It is intended that the scope of the invention be defined by the claims appended hereto.

We claim:

1. A system for detecting objects in a turbid media comprising:

means for directing a pulse of radiant energy into the media, the energy exiting the media as an image-bearing probe beam;

gating signal means for providing a short duration gating pulse having a delay with respect to said pulse of radiant energy;

a first optical parametric amplifier having the probe beam as an input and the gating pulse as a pump beam, the pump beam being temporally and spatially overlapped with the probe beam to produce an amplifier output having gain as a result of a three-wave parametric interaction; and means for detecting the output from said amplifier.

2. The system of claim 1 wherein the amplifier output is frequency shifted from the frequency of the probe beam.

3. The system of claim 2 wherein said means for directing comprises a laser.

4. The system of claim 1 wherein said gating signal means comprises an optical delay circuit having as an input a portion of said pulse of radiant energy.

5. The system of claim 3 wherein said means for directing a pulse of radiant energy comprises a second optical parametric amplifier, a pump input of said second amplifier receiving a time-delayed harmonic of said laser output, a signal input of said second amplifer receiving coherent white light generated from said laser output, wherein changes in said delay cause changes in the output frequency of said amplifier.

6. The system of claim 5 wherein said laser pulse is about 800 nm and the output of said amplifier is variable from 470–2400 nm.

7. The system of claim 6 wherein said second amplifier is operated in a double pass collinear configuration.

8. The system of claim 7 wherein each amplifier comprises a $\beta$-barium borate type I crystal.

9. The system of claim 8 wherein said means for detecting an output comprises binary optic Hartmann sensor means for determining optical phase distortion of the output relative to a calibration file; wherein said sensor detects refractive index changes in the media.

10. The system of claim 8 wherein said gate means is located opposite the turbid media from said means for directing a pulse of radiant energy.

11. The system of claim 1 wherein said gate means is located opposite the turbid media from said means for directing a pulse of radiant energy.

* * * * *